United States Patent
Sasaki

(10) Patent No.: US 7,034,270 B2
(45) Date of Patent: Apr. 25, 2006

(54) SCANNING LASER MICROSCOPE HAVING A SPECTRUM IMAGE POSITIONAL CORRECTION

(75) Inventor: Hiroshi Sasaki, Tokyo (JP)

(73) Assignee: Olympus Corporation, Tokyo (JP)

( * ) Notice: Subject to any disclaimer, the term of this patent is extended or adjusted under 35 U.S.C. 154(b) by 177 days.

(21) Appl. No.: 10/798,013

(22) Filed: Mar. 11, 2004

(65) Prior Publication Data

US 2004/0195497 A1   Oct. 7, 2004

(30) Foreign Application Priority Data

Mar. 13, 2003   (JP)   ............... 2003-067983

(51) Int. Cl.
*G02B 7/04* (2006.01)

(52) U.S. Cl. ............... 250/201.3; 250/208.1; 250/216

(58) Field of Classification Search ............... None
See application file for complete search history.

(56) References Cited

U.S. PATENT DOCUMENTS 6,396,053 B1 * 5/2002 Yokoi ............... 250/234
6,614,526 B1   9/2003 Engelhardt

FOREIGN PATENT DOCUMENTS

JP   2000-56244 A   2/2000

* cited by examiner

*Primary Examiner*—Que T. Le
(74) *Attorney, Agent, or Firm*—Frishauf, Holtz, Goodman & Chick, P.C.

(57) ABSTRACT

In case of irradiating a sample with laser beam, dispersing light emitted from the sample to a spectrum, and fetching and detecting from a wavelength band extraction portion light in at least one band area from the dispersed spectrum, when at least one of a plurality of optical elements arranged between the sample and the dispersive element is switched, a positional relationship between the wavelength band extraction portion and a spectrum image formation position which is displaced in a dispersion direction due to a change in angle of light entering the dispersive element.

38 Claims, 3 Drawing Sheets

SCANNING LASER MICROSCOPE HAVING A SPECTRUM IMAGE POSITIONAL CORRECTION

CROSS-REFERENCE TO RELATED APPLICATIONS

This application is based upon and claims the benefit of priority from prior Japanese Patent Application No. 2003-067983, filed Mar. 13, 2003, the entire contents of which are incorporated herein by reference.

BACKGROUND OF THE INVENTION

1. Field of the Invention

The present invention relates to a scanning laser microscope which condenses laser beam by using an object lens, irradiates a sample with spot light of the condensed laser beam, spectral-decomposes light such as fluorescence from the sample, and detects fluorescence in an arbitrary band area from the obtained spectrum or acquire spectral data.

2. Description of the Related Art

A scanning laser microscope can excite a fluorescent reagent by irradiating a sample dyed to the fluorescent reagent with laser beam, spectral-decomposes fluorescence emitted from the sample, and detect the fluorescent in an arbitrary band area from the obtained spectrum or acquire spectral data of the fluorescence from the spectrum. Such a scanning laser microscope is disclosed in, e.g., U.S. publication No. 6614526 and Jpn. Pat. Appln. KOKAI Publication No. 2000-56244.

U.S. Publication No. 6614526 discloses the following technique. Fluorescence from a sample is dispersed by using a prism, the dispersed fluorescence is condensed by using a focusing optical system so as to enter a slit/detector arrangement. The slit/detector arrangement has a reflection surface forming a slit aperture diaphragm, divides the fluorescence condensed by the focusing optical system into a plurality of partial beam corresponding to respective spectral areas by using the reflection surface, and forms images of the respective partial beam in respective detectors. The slit/detector arrangement can vary a band area to be assigned to each detector by driving and controlling the reflection surface forming the slit aperture diaphragm.

Jpn. Pat. Appln. KOKAI Publication No. 2000-56244 discloses the following technique. Fluorescence from a sample is image-formed in a spectrum form by using a combination of a diffraction grating and a concave mirror or a combination of a prism and a condenser lens. An array of light-deflecting micro mirrors (which will be referred to as a DMD hereinafter) is arranged at this image formation position.

The DMD is composed of a plurality of micro mirrors in an array form. The DMD has a structure capable of electrically switching an angle of a reflection surface of each micro mirror, i.e., switching a reflection direction between two directions. The DMD selects a band area of image-formed fluorescence in a spectrum form. The fluorescence in the selected band area enters a photodetector. In Jpn. Pat. Appln. KOKAI Publication No. 2000-56244, a photodetector is arranged to at least one of two reflection directions of the DMD, and light in an arbitrary band area are led to the photodetector from a spectrum image-formed on the micro mirror. Further, in Jpn. Pat. Appln. KOKAI Publication No. 2000-56244, spectral characteristics of fluorescence can be detected by sequentially switching the micro mirrors.

The scanning laser microscope uses a beam splitter in order to separate laser beam as exciting light and fluorescence from a sample. In the scanning laser microscope, a plurality of types of beam splitters are prepared in accordance with wavelength characteristics of laser wavelengths and fluorescence used for observation. Any one of the plurality of beam splitters is arranged on a light path in accordance with observation of a sample.

For example, when a fluorescent reagent of a sample is excited with Ar laser beam having a wavelength of 488 nm in order to obtain fluorescence having a wavelength of 500 nm to 600 nm, there is used a dichroic beam splitter having characteristics which reflect light having a wavelength of 488 nm and transmit a band area with a wavelength of 500 nm to 600 nm therethrough.

When a fluorescent reagent of a sample is excited with Ar laser beam having a wavelength of 515 nm in order to obtain fluorescence having a wavelength of 530 nm to 650 nm, there is used a dichroic beam splitter having characteristics which reflect light having a wavelength of 515 nm and transmit a band area with a wavelength of 530 nm to 650 nm therethrough.

The plurality of beam splitters are provided to a turret formed into, e.g., a discoid shape. The turret rotates around a rotary bearing portion. The turret arranges any one beam splitter on an optical axis by a switching operation based on rotation.

The turret has a manufacture error in swing of the rotary bearing portion, flatness of a surface on which the plurality of beam splitters are provided and others. Therefore, when the beam splitters are switched by rotating the turret, an angle of a reflection surface relative to the optical axis of each beam splitter differs depending on each beam splitter. It is to be noted that such an angle is referred to as an angular difference between the respective beam splitters.

Since there is an angular difference between the respective beam splitters, when the beam splitters are switched, light from a sample are transmitted through the beam splitter, and an angle of light which enter a dispersive element such as a prism varies. As a result, a spectrum image position obtained by dispersion by the dispersive element and condensation by a condenser lens is displaced in a spectrum direction.

A displacement of the spectrum image formation position will now be described with reference to FIG. 6. A prism 1 disperses incident light 2 of parallel light. The dispersed incident light 2 are condensed by a condenser lens 3. As a result a spectrum is image-formed on an image formation surface 4 formed by the condenser lens 3.

A variable slit 5 is arranged on the image formation surface 4. The variable slit 5 can vary a slit width in the same direction as the spectrum direction. The variable slit 5 can move a slit central position in the same direction as the spectrum direction.

A wavelength width to be taken into a photodetector 6 is changed by varying a width of the variable slit 5. A wavelength center of a band area to be taken into the photodetector 6 is changed by moving a slit center of the variable slit 5. Only light in a band area which has been transmitted through the variable slit 5 are detected by the photodetector 6.

As to the prism 1, a glass material thereof is, e.g., PBH8 and a shape thereof is an equilateral triangle. The incident light 2 enter the prism 1 through a beam splitter. The incident light 2a has a wavelength of, e.g., 510 nm (refractive index: 1.730774), and enter the prism 1 at an angle of 60° relative to a normal line $a_1$ of an incident surface of the prism 1. An outgoing radiation angle of outgoing light 7a emitted from the prism 1 is 59.85° relative to a normal line $a_2$ of an outgoing radiation surface.

When the beam splitter is switched to another beam splitter, the incident light 2b which enter the prism 1 through the beam splitter shifts at angle of, e.g., 6' relative to an optical axis of the incident light 2a. Therefore, an outgoing radiation angle of outgoing light 7b emitted from the prism 1 is 59.75° relative to the normal line $a_2$ of the outgoing radiation surface.

The spectrum image formation position depends on only an angle of outgoing light if the light which enter the condenser lens 3 are parallel light. On the image formation surface 4, a first spectrum image formation position obtained when the incident light 2a having a wavelength of 510 nm enter is different from a second spectrum image position obtained when the incident light 2b having the same wavelength but a different incident angle enter.

For example, assuming that a focal distance of the condenser lens 3 is 30 mm, a displacement quantity ΔL between the first and second spectrum image positions can be represented by the following expression.

$$\Delta L = (\tan 59.85° - \tan 59.75°) \times 30 \quad (1)$$
$$= 0.207 \text{ mm}$$

On the contrary, a wavelength of light outgoing at an angle of the outgoing light 7a (outgoing at 59.85° relative to the normal line $a_2$ of the outgoing radiation surface) before switching the beam splitter with the light which have entered at an angle of the incident light 2b is 505 nm (refractive index: 1.731626).

Therefore, when the beam splitter is switched to another beam splitter in a state that a slit central position of the variable slit 5 is set to a wavelength of 510 nm, a wavelength at the slit central position of the variable slit 5 is 505 nm. As a result, the wavelength of the light which are transmitted through the variable slit 5 and detected by the photodetector 6 is shifted by 5 nm from 510 nm to 505 nm.

In order to spectral-decompose fluorescence emitted from a sample and obtain spectral data of fluorescence from a spectrum, a width of a band area to be taken out is reduced by setting a slit width of the variable slit 5 to be narrow, and a change in light intensity in a spectrum direction is detected while moving the variable slit 5 in the spectrum direction. Therefore, even a small displacement of the spectrum image position affects an accuracy of spectral data. A displacement of the spectrum image position is a serious problem when obtaining accurate spectral data.

BRIEF SUMMARY OF THE INVENTION

A scanning laser microscope according to a main aspect of the present invention comprises: a laser beam source which outputs laser beam; a dispersive element which disperses light emitted from a sample when irradiating the sample with the laser beam and makes spectrum; an image formation element which forms an image of the spectrum made by the dispersive element; a wavelength band extraction portion which is arranged in the vicinity of the image position of the spectrum formed by the image formation element and extract light in at least one wavelength band from the spectrum; at least one photodetector which detects the light in the wavelength band extracted by the wavelength band extraction portion; at least one optical element which is selectively arranged between the sample and the dispersive element; and a correction portion which corrects a positional relationship between the wavelength band extraction portion and a position of the spectrum image which is displaced in the dispersion direction due to a change in an angle of the light entering the dispersive element caused by switching the optical element.

DETAILED DESCRIPTION OF THE INVENTION

A first embodiment according to the present invention will now be described hereinafter with reference to the accompanying drawings.

Figure 1:
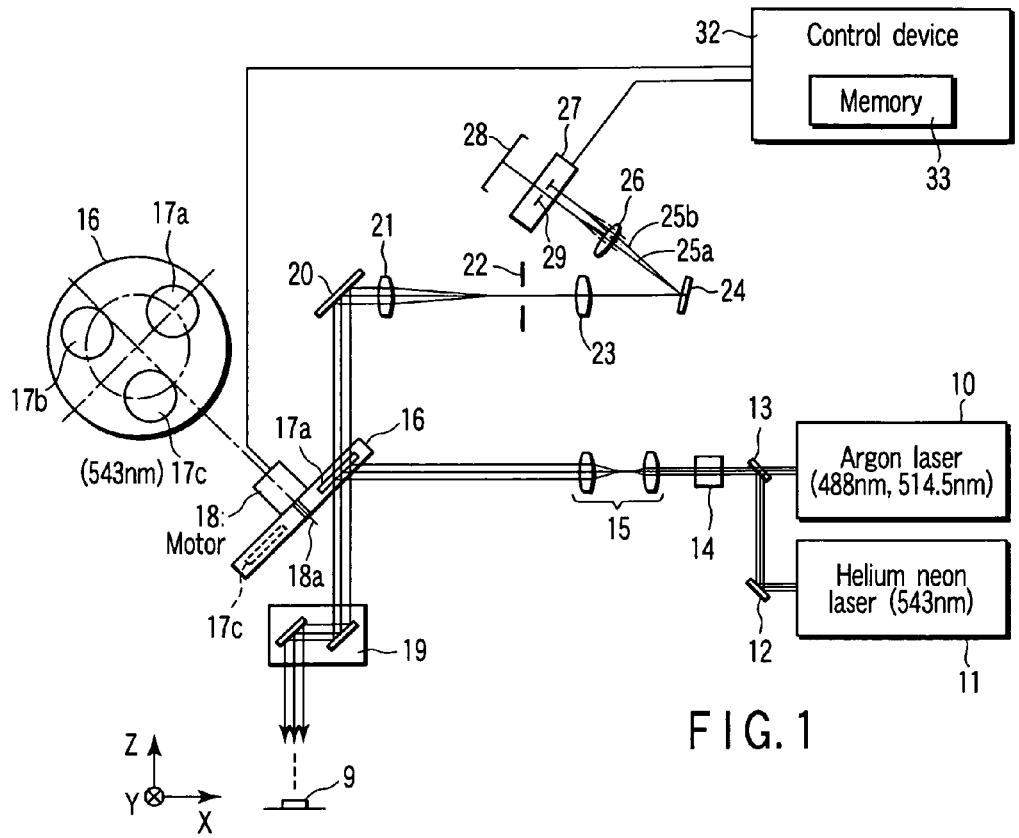
FIG. 1 is a structural view showing a first embodiment of a scanning laser microscope according to the present invention.

FIG. 1 is a structural view of a scanning laser microscope. An argon laser 10 outputs laser beam having wavelengths of 488 nm and 514.5 nm. A helium neon laser 11 outputs laser beam having a wavelength of 543 nm.

A mirror 12 is provided on a light path of laser beam outputted from the helium neon laser 11. A beam-combining dichroic mirror 13 is provided at an intersection between a light path of laser beam outputted from the argon laser 10 and a reflection light path of the mirror 12. The beam-combining dichroic mirror 13 combines laser beam outputted from the argon laser 10 and laser beam outputted from the helium neon laser 11 on one light path.

An acousto-optic tunable filter (which will be referred to as an AOTF hereinafter) 14 and a beam expander 15 are provided on the light path of the laser beam combined and emitted by the beam-combining dichroic mirror 13. The AOTF 14 selects laser beam having at least one wavelength from laser beam having a wavelength of 488 nm, laser beam having a wavelength of 514.5 nm and laser beam having a wavelength of 543 nm. The AOTF 14 independently emphasizes an intensity of each type of laser beam in accordance with respective wavelengths of 488 nm, 514.5 nm and 543 nm.

The beam expander 15 expands a beam diameter of the laser beam to an appropriate diameter.

A beam splitter turret 16 is provided on a light path of the laser beam which have been transmitted through the beam expander 15. The beam splitter turret 16 is formed into a discoid shape as shown in a front view in FIG. 1. A plurality of attachment holes, e.g., three attachment holes are provided on the same circumference on a discoid surface of the beam splitter turret 16 at equal intervals.

A plurality of exciting dichroic mirrors, e.g., three exciting dichroic mirrors 17a, 17b, 17c are attached to the respective attachment holes. The respective exciting dichroic mirrors 17a, 17b, 17c reflect the laser beam from the beam expander 15 in a direction of a sample 9 and transmit fluorescence from the sample 9 therethrough.

The exciting dichroic mirror 17a is used when observing fluorescence from the sample 9 by using laser beam having a wavelength of 488 nm as exciting light. The exciting dichroic mirror 17a has characteristics to reflect light having a wavelength of 488 nm and transmit light having a wavelength of 500 to 620 nm therethrough.

The exciting dichroic mirror 17b is used when observing fluorescence from the sample 9 by using laser beam having a wavelength of 514.5 nm as exciting light. The exciting dichroic mirror 17b has characteristics to reflect light having a wavelength of 514.5 nm and transmit light having a wavelength of 525 to 620 mm therethrough.

The exciting dichroic mirror 17c is used when observing fluorescence from the sample 9 by using laser beam having a wavelength of 543 nm as exciting light. The exciting dichroic mirror 17c has characteristics to reflect light having a wavelength of 543 nm and transmit light having a wavelength of 555 to 620 nm therethrough.

The beam splitter turret 16 is provided on a tilt at substantially 45° relative to an optical axis of laser beam which have been transmitted through the beam expander 15. A rotary shaft of a motor 18 is provided at the center of the beam splitter turret 16. The beam splitter turret 16 rotates around a rotary shaft 18a by a rotating operation of the motor 18. The beam splitter turret 16 rotates and switches one exciting dichroic mirror 17a, 17b or 17c according to observation of the sample 9 from the respective exciting dichroic mirrors 17a to 17c to the light path of the laser beam and fluorescence.

A galvanometer scanner 19 is provided on a reflection light path of the exciting dichroic mirror 17a, 17b or 17c. The galvanometer scanner 19 two-dimensionally scans the laser beam on the sample 9 by deflecting the laser beam reflected on the exciting dichroic mirrors 17a, 17b or 17c in different directions, i.e., a direction X and a direction Y.

It is to be noted that a non-illustrated condenser lens or the like is provided on a light path of a scanning output from the galvanometer scanner 19. The condenser lens condenses the laser beam and forms spot light on a surface of the sample 9.

On the other hand, a reflection mirror 20 is provided on a transmission light path of the exciting dichroic mirror 17a, 17b or 17c. A confocal lens 21, a confocal pinhole 22, a collimator lens 23 and a diffraction grating 24 are provided on a reflection light path of the reflection mirror 20.

The diffraction grating 24 performs wavelength dispersion of incident fluorescence which has been transmitted through the collimator lens 23. The diffraction grating 24 reflects fluorescence having a wavelength of, e.g., 500 nm in a direction of reflected light 25a, and reflects fluorescence having a wavelength of, e.g., 600 nm in a direction of reflected light 25b. Each of the fluorescence having the wavelengths of 500 nm and 600 nm is reflected at an angle between the reflected light 25a and the reflected light 25b in accordance with the wavelengths. That is, the diffraction grating 24 makes spectrum fluorescence light.

A condenser lens 26, a variable slit unit 27 and a photodetector 28 are provided on the reflected light path of the diffraction grating 24. The variable slit unit 27 has a variable slit which can vary a slit width ΔM.

Figure 2:
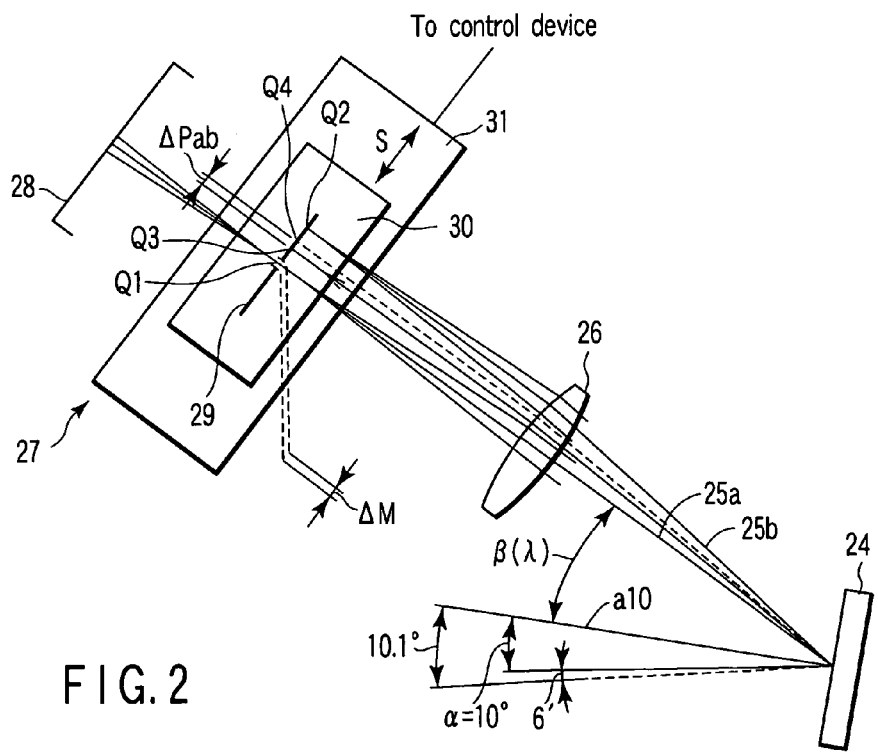
FIG. 2 is a structural view of a variable slit unit in the first embodiment of the scanning laser microscope according to the present invention.

As shown in FIG. 2, the variable slit 29 is provided at an image formation position of the condenser lens 26 on a slit width variable portion 30. A widthwise direction of the slit width ΔM of the variable slit 27 is caused to match with a spectral dispersion direction.

The slit width variable portion 30 has an electric drive portion which variably controls the slit width ΔM of the variable slit 29. As a result, the slit width variable portion 30 controls a wavelength width of fluorescence which is fetched from a spectrum and enters the photodetector 28 by variably controlling the slit width ΔM of the variable slit 29.

The slit width variable portion 30 is provided on an electro-motive stage 31. The electro-motive stage 31 enables movement of the slit width variable portion 30 in the same direction (direction indicated by arrows S) as a spectrum direction formed by dispersion of fluorescence by the diffraction grating 24.

The variable slit unit 27 moves the slit width variable portion 30 in the direction indicated by arrows S by drive of the electro-motive stage 31. As a result, the variable slit 29 moves in the same direction as the spectrum direction. Consequently, a wavelength center of fluorescence detected by the photodetector 28 is controlled.

The photodetector 28 detects a light intensity of incident fluorescence, and outputs a detection signal according to this light intensity.

A control device 32 controls the motor 18 of the beam splitter turret 16 to rotate. The control device 32 controls one exciting dichroic mirror 17a, 17b or 17c of the respective exciting dichroic mirrors 17a to 17c to be switched on the light path of the laser beam and the fluorescence.

The control device 32 corrects a positional relationship between the variable slit 29 and a spectrum image position which is displaced in a dispersion direction of the diffraction grating 24 due to switching of each exciting dichroic mirror 17a, 17b or 17c.

The control device 32 has a memory 33 which previously stores a plurality of correction quantities corresponding to respective displacements of spectrum image positions relative to the respective exciting dichroic mirrors 17a, 17b and 17c. The plurality of correction quantities are formed into a table (which will be referred to as a variable slit control table hereinafter) in accordance with the respective exciting dichroic mirrors 17a, 17b and 17c and stored in the memory 33.

Therefore, in cooperation with the switching the exciting dichroic mirror 17a, 17b or 17c, the control device 32 reads a correction quantity relative to the exciting dichroic mirror 17a, 17b or 17c from the variable slit control table in the memory 33, and transmits a correction signal indicative of the correction quantity to the variable slit unit 27. As a result, the variable slit unit 27 moves the variable slit 29 of the variable slit unit 27 in the spectrum direction, and performs a positional correction with respect to the spectrum image formation position.

An operation of the apparatus having the above structure will now be described.

The argon laser 10 outputs laser beam having wavelengths of 488 nm and 514.5 nm. The laser beam outputted from the argon laser 10 enter the beam-combining dichroic mirror 13.

At the same time, the helium neon laser 11 outputs laser beam having a wavelength of 543 nm. The laser beam outputted from the helium neon laser 11 are reflected on the mirror 12, and enter the beam-combining dichroic mirror 13.

The beam-combining dichroic mirror 13 combines laser beam outputted from the argon laser 10 with laser beam outputted from the helium neon laser 11 on one light path. The laser beam combined by the beam-combining dichroic mirror 13 enter the AOTF 14.

The AOTF 14 selects laser beam having at least one of wavelengths 488 nm, 514.5 nm and 543 nm, e.g., the wavelength of 488 nm, and modulates an intensity of the laser beam. The laser beam having the wavelength of 488 nm selected by the AOTF 14 are expanded to have an appropriate beam diameter by the beam expander 15, and enter the beam splitter turret 16.

For example, when observing fluorescence from the sample 9 by using the laser beam having a wavelength of 488 nm as exciting light, the beam splitter turret 16 provides the exiting dichroic mirror 17a selected from the three exciting dichroic mirrors 17a, 17b, 17c on the light path.

The laser beam having the wavelength of 488 nm which have entered the exciting dichroic mirror 17a are reflected on the exciting dichroic mirror 17a, and enter the galvanometer scanner 19. The laser beam having the wavelength of 488 nm are deflected in the direction X and the direction Y by the galvanometer scanner 19, and two-dimensionally scanned on the sample 9.

A fluorescent reagent dyed in the sample is excited by irradiation of the laser beam having the wavelength of 488 nm. The fluorescence having a wavelength of, e.g., 500 nm to 600 nm is emitted from the sample 9 by this excitation. This fluorescence is transmitted through the exciting dichroic mirror 17a from the galvanometer scanner 19 and enters the reflection mirror 20. The fluorescence is reflected by the reflection mirror 20 and enters the confocal lens 21. Further, the fluorescence is condensed by the confocal lens 21, transmitted through the confocal pinhole 22, converted into parallel light by the collimator lens 23, and enters the diffraction grating 24.

The diffraction grating 24 performs wavelength dispersion of the fluorescence of the incident parallel light. The diffraction grating 24 reflects the fluorescence having a wavelength of, e.g., 500 nm in a direction of reflected light 25a, and reflects the fluorescence having a wavelength of 600 nm in is a direction of reflected light 25b.

The fluorescence having the wavelength of 500 nm and the fluorescence having the wavelength of 600 nm are respectively condensed by the condenser lens 26. As a result, each spectrum of the fluorescence having the wavelength of 500 nm and the fluorescence having the wavelength of 600 nm is formed.

For example, when obtaining a fluorescent band area with a wavelength of 500 nm, the variable slit 29 is moved by movement of the slit width variable portion 30 in the same direction (indicated by arrows S) as a spectrum direction caused by the electromotive stage 31. A slit central position of the variable slit 29 is arranged on a coordinate $Q_1$ by this movement as shown in FIG. 2. When acquiring a fluorescent band area having a wavelength of 600 nm, the slit central position of the variable slit 29 is arranged on a coordinate $Q_2$. The slit central position of the variable slit 29 is set in accordance with the thus obtained fluorescent band area.

Giving a concrete description with reference to FIG. 2, it is assumed that an angle of the light entering the diffraction grating 24 is α (e.g., 10°) with respect to a normal line $a_{10}$ of the incident surface of the diffraction grating 24, for example. It is presumed that an angle of the light having a wavelength λ reflected on the diffraction grating 24 is β (λ) with respect to the normal line $a_{10}$. Assuming that the number of stripes of the diffraction grating 24 is N and an order of diffraction rays to be fetched is m, the following relational expression can be achieved:

$$\sin \alpha + \sin(-\beta) = N \cdot m \cdot \lambda \quad (2)$$

Here, assuming that m=−1 and N=600/mm, the following expression can be attained:

$$\beta (\lambda) = \sin^{-1}(\sin \alpha + 0.6\lambda) \quad (3)$$

For example, when a wavelength is 500 nm, the reflected light 25a exist on the optical axis of the condenser lens 26. At this moment, it is assumed that an image formation position of the reflected light 25a on the variable slit 29 is, e.g., 0 μm.

Assuming that a focal distance of the condenser lens 26 is, e.g., 40 mm, an image formation position P (λ) for each wavelength can be obtained based on the following expression:

$$P (\lambda) = 40 \tan(\beta(\lambda) - \beta(500 \text{ nm})) \quad (4)$$

Figure 3:
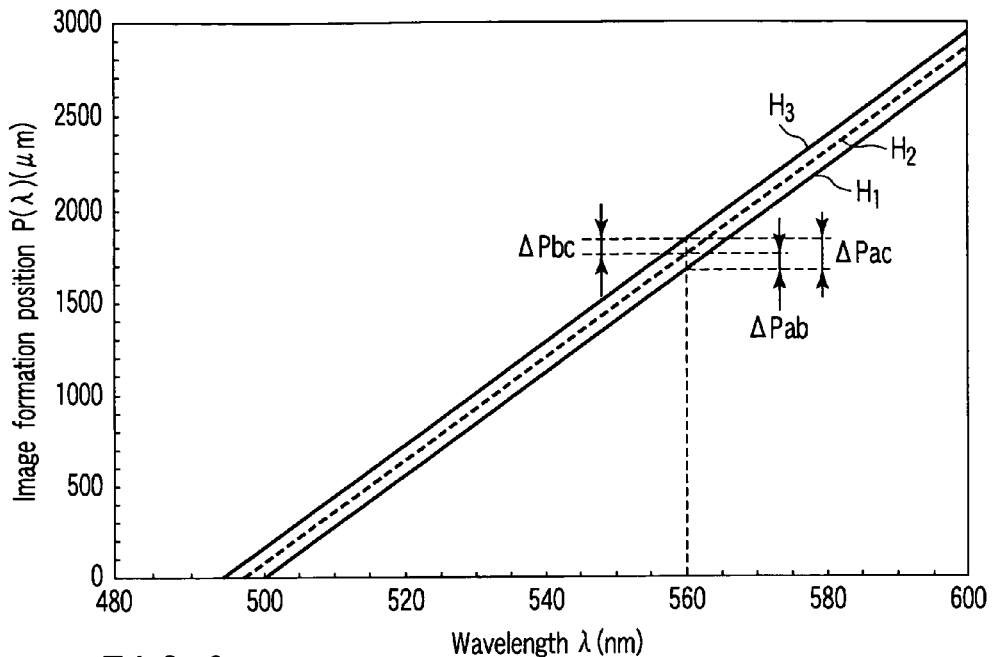
FIG. 3 is a view showing an image formation position on a variable slit in accordance with each wavelength in the first embodiment of the scanning laser microscope according to the present invention.

$H_1$ in FIG. 3 represents an image formation position P (λ) on the variable slit 29 for each wavelength when the exciting dichroic mirror 17a is used, which is obtained by assigning a wavelength λ (unit: nm) in the above-described expression (4). In this drawing, a horizontal axis represents a wavelength λ (unit: nm) and a vertical axis represents an image formation position P (unit: μm).

A description will now be given as to an operation when the exciting dichroic mirror 17a is switched to the exciting dichroic mirror 17b.

The exciting dichroic mirror 17b is used when observing fluorescence from the sample 9 by utilizing laser beam having a wavelength of 514.5 nm as exciting light. The AOTF 14 selects laser beam having a wavelength of 514.5 nm, and emphasizes a light intensity of the laser beam.

When the beam splitter turret 16 is rotated and the exciting dichroic mirror 17a is switched to the exciting dichroic mirror 17b, there is generated an angular difference between the respective exciting dichroic mirrors 17a and 17b.

It is assumed that the respective reflection surfaces of the exciting dichroic mirrors 17a and 17b are displaced at, e.g., an angle of 1.5' in the dispersion direction in the diffraction grating 24 when the exciting dichroic mirror 17a is switched to the exciting dichroic mirror 17b. As a result, the angle of the light which are transmitted through the exciting dichroic mirror 17b is shifted by 3' which is twofold of that when the light are transmitted through the exciting dichroic mirror 17a.

Further, when a focal distance of the confocal lens 21 is determined as 160 mm and a focal distance of the collimator lens 23 is determined as 80 mm, an outgoing radiation angular difference of the collimator lens 23 becomes double, i.e., 6' (0.1°) as compared with the case using the exciting dichroic mirror 17a.

As a result, the angle α of the light entering the diffraction grating 24 becomes 10.1°.

The image formation position P(λ) when switched to the exciting dichroic mirror 17b can be obtained by assigning the angle 10.1° to the angle α of the light entering the diffraction grating 24 in the above-described expression (3) and using the above-mentioned expression (4).

A relationship between each wavelength when using the exciting dichroic mirror 17b and the spectrum image position is represented by a series $H_2$ in FIG. 3. As apparent from the drawing, image positions of the light having the same wavelength, e.g., the wavelength of 560 nm on the variable slit 29 are different from each other by ΔPab (μm) depending on the respective exciting dichroic mirrors 17a and 17b.

Giving a description with reference to FIG. 2, the image formation position of the laser beam having a wavelength of 560 nm is $Q_3$ on the variable slit 29 when the exciting dichroic mirror 17a is used. The image position of the laser beam having a wavelength of 560 nm is $Q_4$ on the variable slit 29 when the exciting dichroic mirror 17b is used. Therefore, the respective image positions $Q_3$ and $Q_4$ produce the displacement ΔPab. Here, the slit width variable portion 30 moves in the same direction as the spectrum based on a correction quantity (variable slit control table) relative to the exciting dichroic mirror 17b stored in the memory 33 in the control device 32. The displacement ΔPab of the variable slit 29 is corrected.

As a result, even if the exciting dichroic mirror 17a is switched to the exciting dichroic mirror 17b, the central position of the variable slit 29 with respect to each wavelength is subjected to a positional correction.

A description will now be given as to the operation when switching the exciting dichroic mirror 17a to the exciting dichroic mirror 17c.

The exciting dichroic mirror 17c is used when observing fluorescence from the sample 9 by utilizing laser beam having a wavelength of 543 nm as exciting light. The AOTF 14 selects laser beam having a wavelength of 543 nm, and emphasizes an intensity of the laser beam.

When the exciting dichroic mirror 17a is switched to the exciting dichroic mirror 17c, there is generated an angular difference between the respective exciting dichroic mirrors 17a and 17c.

For example, in cases where the exciting dichroic mirror 17a is switched to the exciting dichroic mirror 17c, if a dispersion direction of the light in the diffraction grating 24 is shifted by, e.g., an angle of 3', an angle of the light which are transmitted through the exciting dichroic mirror 17c is shifted by 6' which is twofold of that of the case in which the light are transmitted through the exciting dichroic mirror 17a.

When a focal distance of the confocal lens 21 is determined as 160 mm and a focal distance of the collimator lens 23 is determined as 80 mm like the above example, an outgoing radiation angular difference of the collimator lens 23 becomes 12' (0.2°) which is twofold of that when using the exciting dichroic mirror 17a. As a result, an angle α of the light entering the diffraction grating 24 becomes 10.2°.

The image position P (λ) when switched to the exciting dichroic mirror 17c can be obtained by assigning 10.2° in the angle α in the above-described expression (3) and using the above-mentioned expression (4).

A relationship between each wavelength and a spectrum image position when using the exciting dichroic mirror 17c is represented by $H_3$ in FIG. 3. As apparent from the drawing, the image formation position of the light having the same wavelength, e.g., a wavelength of 560 nm on the variable slit 29 differs by a displacement ΔPac (μm) depending on the respective exciting dichroic mirrors 17a and 17c. Here, the slit width variable portion 30 moves in the same direction as the spectrum based on a correction quantity (variable slit control table) with respect to the exciting dichroic mirror 17c stored in the memory 33 of the control device 32. The displacement ΔPbc of the variable slit 29 is likewise corrected.

As a result, even if the exciting dichroic mirror 17a is switched to the exciting dichroic mirror 17c, the central position of the variable slit 29 with respect to each wavelength is subjected to a positional correction by driving of the electro-motive stage 31.

The memory 33 of the control device 32 forms and stores a variable slit control table with respective displacements ΔPab, ΔPac and ΔPbc (displacements when switching between the respective exciting dichroic mirrors 17b and 17c) of the variable slit 29 relative to respective wavelengths when switching between the respective exciting dichroic mirrors 17a, 17b and 17c being used as respective correction quantities.

The control device 32 controls and rotates the motor 18 of the beam splitter turret 16. When switching is performed between the respective exciting dichroic mirrors 17a, 17b and 17c, the control device 32 reads the corresponding correction quantity ΔPab, ΔPac or ΔPbc from the variable slit control table in cooperation with this switching, and transmits a correction signal according to the correction quantity ΔPab, ΔPac or ΔPbc to the variable slit unit 27.

The variable slit unit 27 moves the variable slit 29 in the spectrum direction (direction indicated by arrows S) in accordance with the correction signal. As a result, a position of the variable slit 29 is automatically corrected with respect to the spectrum image position. For example, when the exciting dichroic mirror 17a is switched to the exciting dichroic mirror 17b, the position of the variable slit 29 is automatically corrected in the same direction as the spectrum by the correction quantity ΔPab. As a result, even if the exciting dichroic mirror 17a is switched to the exciting dichroic mirror 17b, the fluorescence including a wavelength of 560 nm is correctly led to the photodetector 28.

As described above, in the first embodiment, the variable slit control table is formed and stored in the memory 33 with the respective displacements ΔPab, ΔPac and ΔPbc when switching between the respective exciting dichroic mirrors 17a, 17b and 17c being used as the respective correction quantities. When switched to the exciting dichroic mirror 17a, 17b or 17c, the corresponding correction quantity ΔPab, ΔPac or ΔPbc is read from the variable slit control table, the variable slit 29 is moved in the spectrum direction in accordance with the correction quantity ΔPab, ΔPac or ΔPbc, and a position of the variable slit 29 is automatically corrected with respect to the spectrum image position.

As a result, even if an angular difference is generated on the reflection surface when the exciting dichroic mirror is switched, measurement for each band area can be accurately performed without being affected by this angular displacement.

When acquiring spectral data, a width of a band area to be fetched is reduced by setting a slit width of the variable slit 5 narrow in order to increase a wavelength resolution of the data. Therefore, even a small displacement of the spectrum image position affects acquisition of the spectral data. On the contrary, since a position of the variable slit 29 is automatically corrected with respect to the spectrum image position irrespective of a type of the exciting dichroic mirrors to be used, a band area to be fetched from the spectrum matches with a band area to be actually fetched, thereby assuring the accuracy of the spectral data.

It is to be noted that the means for fetching a band area which is detected by the photodetector 28 is not restricted to the variable slit 29 in the first embodiment. For example, as disclosed in Jpn. Pat. KOKAI Publication No. 2000-56244, the photodetector is arranged on one reflected light path among a plurality of reflected light paths from the DMD arranged at the spectrum image position, and an arrangement direction of each dimensionless mirror of the DMD is controlled. As a result, a band area which is detected by the photodetector 28 can be controlled. In this case, when switched to the exciting dichroic mirror 17a, 17b or 17c, an address of each dimensionless mirror of the DMD corresponding to each wavelength is changed in accordance with the spectrum image position.

Furthermore, in regard to the means for fetching a band area which is detected by the photodetector 28, respective light paths may be divided in accordance with each band area by using the slit and each mirror as disclosed in U.S. Publication No. 6614526. In this case, each coordinate of the slit and the mirror is offset in accordance with each of the exciting dichroic mirrors 17a, 17b and 17c like the first embodiment.

Respective optical elements which make a spectrum and form an image are not restricted to the diffraction grating 24 and the condenser lens 26. For example, as disclosed in Jpn. Pat. Appln. KOKAI Publication No. 2000-56244, a prism may be combined with the condenser lens, or a plane diffraction grating may be combined with a concave mirror, or a concave diffraction grating may be used.

A second embodiment according to the present invention will now be described with reference to the accompanying drawings.

Figure 4:
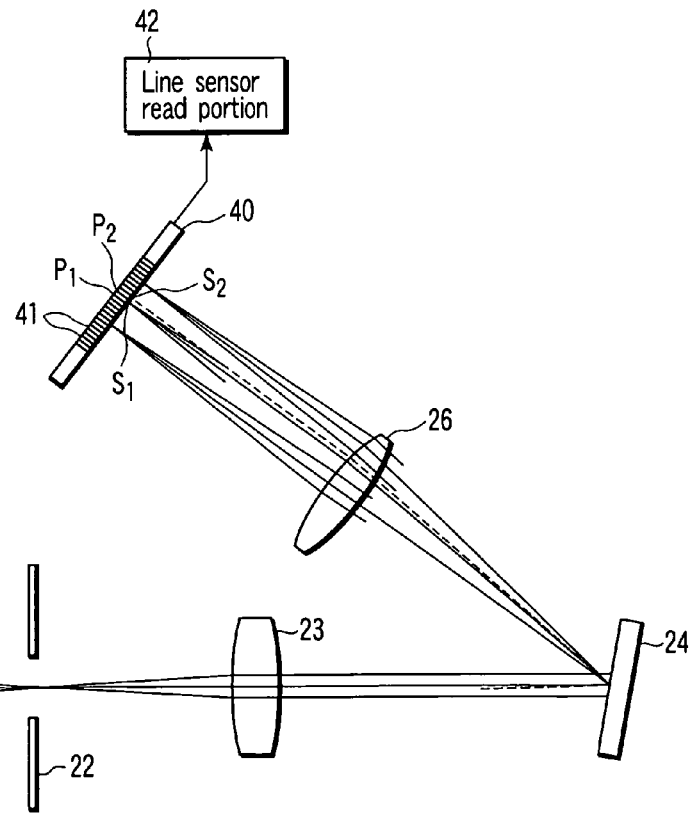
FIG. 4 is a structural view showing a characteristic part in a second embodiment of a scanning laser microscope according to the present invention.

FIG. 4 is a structural view showing a characteristic part in a scanning laser microscope. It is to be noted that any other parts are equal to those depicted in the structural view of FIG. 1. In the scanning laser microscope, a line sensor (photodetector) 40 is provided in place of the variable slit unit 27 and the photodetector 28 in the first embodiment.

The line sensor 40 is constituted by arranging a plurality of light receiving pixels (detection portions) 41 in an array form. The line sensor 40 is arranged at a spectrum image formation position. The line sensor 40 is provided in a direction along which an arrangement direction of the respective light receiving pixels 41 matches with the spectrum direction.

An arrangement position of each light receiving pixel 41 corresponds to a band area of each spectrum. Therefore, a necessary band area can be fetched by selecting a light receiving pixel 41 which enables light reception of the light and a light receiving pixel 41 which disables the same from the respective light receiving pixels 41.

A line sensor read portion 42 selects the light receiving pixel 41 which enables light reception of the light and the light receiving pixel 41 which disables the same in the line sensor 40, and reads a light detection value from each light receiving pixel 41 which enables light reception.

The line sensor read portion 42 previously stores a plurality of correction quantities corresponding to respective displacements of the spectrum image position in accordance with the respective exciting dichroic mirrors 17a, 17b and 17c. The line sensor read portion 42 reads a correction quantity relative to the exciting dichroic mirror 17a, 17b or 17c to be switched in the operation to switch to the exciting dichroic mirror 17a, 17b or 17c, and selects the light receiving pixel 41 which enables light reception and the light receiving pixel 41 which disables the same in accordance with the correction quantity. That is, the line sensor read portion 42 corrects each pixel position.

It is to be noted that the line sensor read portion 42 may be provided in the control device 32. As a result, the control device 32 selects the light receiving pixel 41 which directly enables light reception of light and the light receiving pixel 41 which disables the same with respect to the line sensor 40.

The operation of the apparatus having such a structure will now be described.

When switched to the exciting dichroic mirror 17a, 17b or 17c, the spectrum image formation position on the line sensor 40 is displaced due to an angular difference between respective reflection surfaces of the exciting dichroic mirrors 17a, 17b and 17c. For example, when the exciting dichroic mirror 17a is provided on the light path, an image formation position of fluorescence having a center wavelength of 560 nm is $S_1$. When the exciting dichroic mirror 17b is provided on the light path, an image formation position of the fluorescence having the center wavelength of 560 nm is $S_2$.

As a result, when the exciting dichroic mirror 17a is provided on the light path, a position of the light receiving pixel 41 which detects the fluorescence having the wavelength of 560 nm is $P_1$. When the exciting dichroic mirror 17b is provided on the light path, a position of the light receiving pixel 41 which detects the fluorescence having the wavelength of 560 nm is $P_2$. Therefore, when detecting the fluorescence having the center wavelength of 560 nm, a displacement quantity of the light receiving pixel 41 when switching from the exciting dichroic mirror 17a to the exciting dichroic mirror 17b corresponds to a distance between the position $P_1$ and the position $P_2$.

A memory 33 of a control device 32 stores a displacement quantity between the respective positions $P_1$ and $P_2$ of the respective light receiving pixels 41 when switching from the exciting dichroic mirror 17a to the exciting dichroic mirror 17b as a pixel correction quantity. Incidentally, it is needless to say that the memory 33 stores each pixel correction quantity when switching between the respective exciting dichroic mirrors 17a, 17b and 17c.

When switching between the respective exciting dichroic mirrors 17a, 17b and 17c, the control device 32 reads a pixel correction quantity from the memory 33 in cooperation with switching, and transmits a pixel read position correction signal according to the correction quantity to the line sensor read portion 42.

The line sensor read portion 42 selects a light receiving pixel 41 which enables light reception of fluorescence and a light receiving pixel 41 which disables the same in the line sensor 40 in accordance with the correction quantity, and reads a light detection value from the light receiving pixel 41 which has enabled light reception.

For example, when the exciting dichroic mirror 17a is switched to the exciting dichroic mirror 17b, the line sensor read portion 42 corrects a position of the light receiving pixel 41 which enables light reception of fluorescence having a wavelength of 560 nm to $P_1$ to $P_2$.

As described above, in the second embodiment, the light receiving pixel 41 which enables light reception of fluorescence and the light receiving pixel 41 which disables the same in the line sensor 40 are corrected in accordance with a pixel correction quantity corresponding to each displacement of the spectrum image formation position when switching between the respective exciting dichroic mirrors 17a, 17b and 17c. As a result, like the first embodiment, measurement for each band area can be accurately performed, thereby measuring highly accurate spectral data.

It is to be noted that the line sensor 40 is used in the second embodiment, but the present invention is not restricted thereto, and a CCD, a multi-channel photo multiplier or the like may be used.

A third embodiment according to the present invention will now be described with reference to the accompanying drawings. It is to be noted that like reference numerals denote parts equal to those in FIG. 1, thereby eliminating their detailed explanation.

Figure 5:
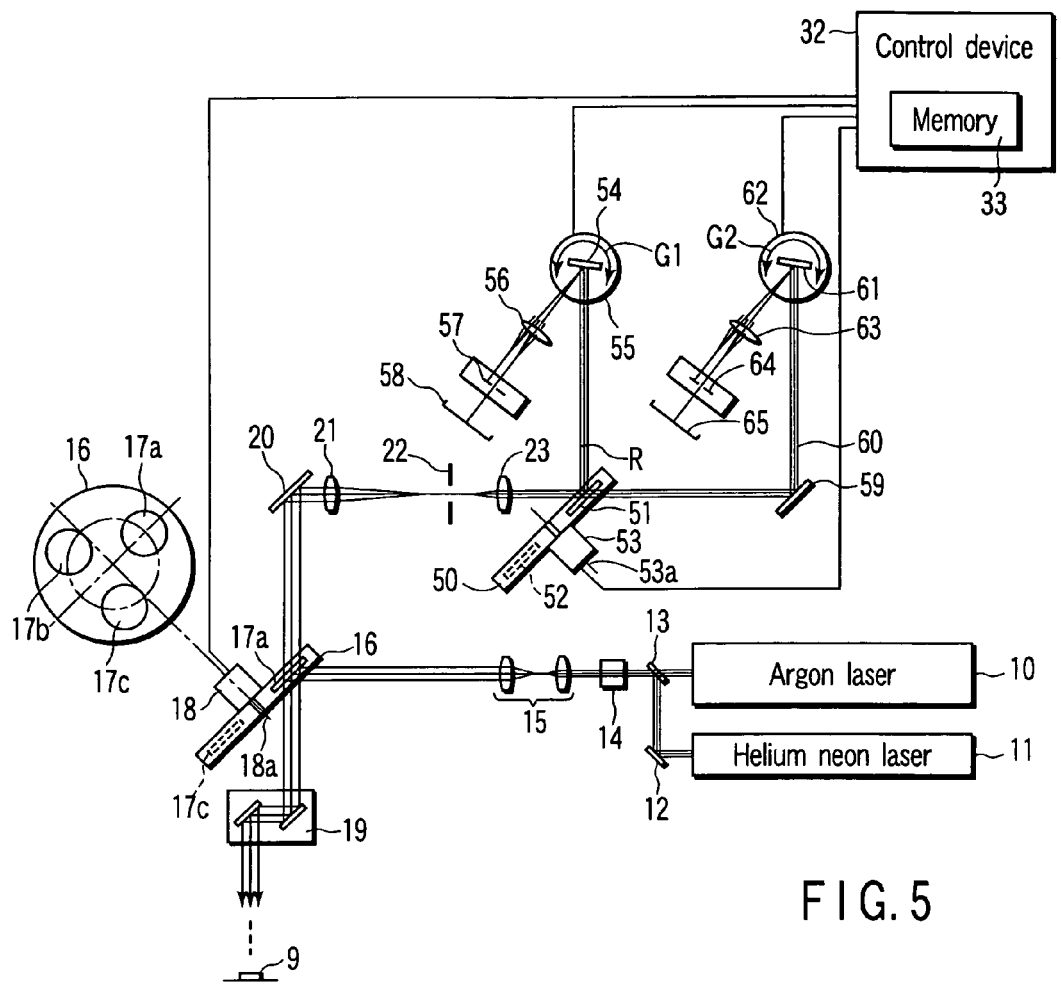
FIG. 5 is a structural view showing a third embodiment of a scanning laser microscope according to the present invention.
Figure 6:
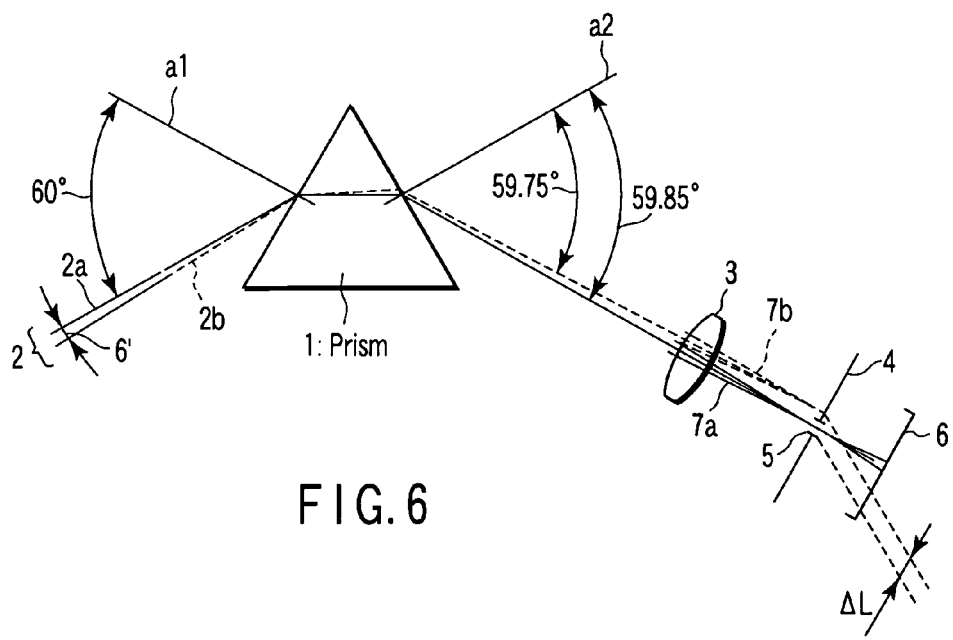
FIG. 6 is a view illustrating a displacement of a spectrum image formation position on a photodetector in a conventional scanning laser microscope.

FIG. 5 is a structural view showing a scanning laser microscope. A spectral beam splitter turret 50 is provided on a light path of light which have been transmitted through a collimator lens 23. The spectral beam splitter turret 50 is formed into a discoid shape. In the spectral beam splitter turret 50, a plurality of attachment holes, e.g., three attachment holes are provided on the same circumference at equal intervals.

A spectral dichroic mirror (second beam splitter) 51 and a reflection mirror 52 are attached to two attachment holes in the plurality of attachment holes. The reflection mirror 52 reflects all the light. It is to be noted that respective exciting dichroic mirrors 17a to 17c attached to the beam splitter turret 16 are determined as first beam splitters.

The spectral dichroic mirror 51 divides the light into reflected light and transmitted light in accordance with each wavelength. The spectral dichroic mirror 51 reflects fluorescence having a center wavelength shorter than, e.g., a center wavelength of 550 nm, and transmits fluorescence having a wavelength longer than a center wavelength of 550 nm therethrough.

The remaining attachment hole in the spectral beam splitter turret 50 is a vacant hole, and it transmits all the light therethrough.

It is to be noted that the reflection mirror 52 is defined as a beam splitter with a ratio of a reflectivity and a transmissivity being approximately 100%:0% and the vacant hole is defined as a beam splitter with a ratio of a reflectivity and a transmissivity being approximately 0%:100%.

The spectral beam splitter turret 50 is provided on a slant at approximately 45° relative to an optical axis of fluorescence transmitted through the collimator lens 23. A rotary shaft of a motor 53 is provided at the center of the spectral beam splitter turret 50. Therefore, the spectral beam splitter turret 50 rotates around a rotary shaft 53a by a rotating operation of the motor 53. As a result, the spectral beam splitter turret 50 arranges the spectral dichroic mirror 51, the reflection mirror 52 or the vacant hole on the light path.

A diffraction grating 54 is provided on a reflected light path R of the spectral dichroic mirror 51 and the reflection mirror 52. The diffraction grating 54 can rotate in a direction of arrows G1 by an operation of a galvanometer 55.

A condenser lens 56, a width variable slit 57 and the photodetector 58 are provided on a light path of fluorescence dispersed by the diffraction grating 54. The width variable slit 57 is provided at a spectrum image position obtained by the condenser lens 56. The width variable slit 57 can vary only a slit width by using, e.g., a non-illustrated electric drive mechanism.

On the other hand, a reflection mirror 59 is provided on a light path (which will be referred to as a transmitted light path hereinafter) T of light transmitted through the spectral dichroic mirror 51. A diffraction grating 61 is provided on a reflected light path 60 of the reflection mirror 59. The diffraction grating 61 can rotate in a direction of arrows $G_2$ by an operation of a galvanometer 62.

A photodetector 65 is provided on a light path of fluorescence dispersed by the diffraction grating 61. A condenser lens 63 and a width variable slit 64 are provided on a light path of fluorescence between the diffraction grating 61 and the photodetector 65. The width variable slit 64 is provided at a spectrum image formation position obtained by the condenser lens 63. The width variable slit 64 can vary only a slit width by using, e.g., a non-illustrated electric drive mechanism.

The control device 32 performs switching of the respective exciting dichroic mirror 17a, 17b or 17c by using the beam splitter turret 16. The control device 32 performs switching of the spectral dichroic mirror 51, the reflection mirror 52 or the vacant hole by using the spectral beam splitter turret 50. The beam splitter turret 16 and/or the spectral beam splitter turret 50 is switched, an angle of light which enter the diffraction grating 54 and/or 61 is changed due to an angular difference produced due to this switching.

The control device 32 rotate of galvanometer 55 and/or 62, corrects a positional relationship between the width variable slit 57 and/or 64 and a spectrum image position which is displaced in a dispersion direction of light dispersed by the diffraction grating 54 and/or 61 caused due to a change in an angle of incident light on the diffraction grating 54 and/or 61.

A memory 33 of the control device 32 stores a correction quantity of the galvanometer 55 and/or 62 corresponding to the displacement of the spectrum image formation position and the variable slit 57 and/or 64 which is determined based on a combination of the exciting dichroic mirrors 17a, 17b and 17c attached to the beam splitter turret 16 and the spectral dichroic mirror 51, the reflection mirror 52 and the vacant hole attached to the spectral beam splitter turret.

In each operation to switch between the respective exciting dichroic mirrors 17a, 17b and 17c and between the spectral dichroic mirror 51, the reflection mirror 52 and the vacant hole, the control device 32 reads a corresponding correction quantity from the memory 33 in cooperation with switching, drives the galvanometer 55 and/or 62 in accordance with the correction quantity, and corrects the spectrum image position on the width variable slit 57.

An operation of the apparatus having such a structure will now be described.

Switching is performed between the beam splitter turret 16 and the spectral beam splitter turret 50. Since the both members can be independently switched, one of them may be switched and both of them may be simultaneously switched according to circumstances. How the both mirrors are combined is arbitrary.

When switching is performed, a spectrum image formation position formed by the diffraction grating 54 and/or 61 and the condenser lenses 56 and 63 is displaced.

In cooperation with this switching operation, the control device 32 reads from the memory 33 a correction quantity corresponding to a combination of the switched mirrors in accordance with types of the switched mirrors (the exciting dichroic mirrors 17a, 17b and 17c in the beam splitter turret 16, and the spectral dichroic mirror 51, the reflection mirror 52 and the vacant hole in the spectral beam splitter turret 50), and drives the galvanometer 55 and/or the galvanometer 61 to rotate in accordance with this correction quantity.

The light detected by the photo detector 58 through the diffraction grating 54 are affected by switching of both the beam splitter turret 16 and the spectral beam splitter turret 50.

On the other hand, the light detected by the photo detector 65 through the diffraction grating 61 are affected by switching of only the beam splitter turret 16.

Spectral data of fluorescence is acquired from a spectrum obtained by spectral-decomposing the fluorescence emitted from the sample 9. In this case, the respective diffraction gratings 54 and 61 are rotated by the respective galvanometers 55 and 62. As a result, each spectrum image position is moved in a direction of the spectrum.

When acquiring spectral data of the fluorescence, a slit width of each of the width variable slits 57 and 64 must be set narrow in order to increase a wavelength resolution.

In an operation to switch the respective exciting dichroic mirrors 17a, 17b and 17c and the spectral dichroic mirror 51, the reflection mirror 52 and the vacant hole, the control device 32 reads a correction quantity corresponding to each combination in cooperation with switching from the memory 33, and rotates and drives the galvanometer 55 in accordance with the correction quantity.

As a result, an image position of the spectrum dispersed by the diffraction grating 54 and condensed by the condenser lens 56 is corrected. Only light in a band area to be detected are transmitted through the width variable slit 57, and enter the photodetector 58.

As a result, there can be detected spectral data indicative of a change in light intensity of each fluorescence in a spectrum direction.

It is to be noted that the fluorescence entering the diffraction grating 61 is transmitted through the spectral dichroic mirror 51 or transmitted through the vacant hole. Consequently, an angle of light entering the diffraction grating 61 is changed by only switching of the exciting dichroic mirrors 17a, 17b and 17c. Therefore, it is good enough to correct a spectrum image position with respect to the width variable slit 64 only when switching the exciting dichroic mirrors 17a, 17b and 17c.

As described above, in the third embodiment, in the operation to switch between the respective exciting dichroic mirrors 17a, 17b and 17c and between the spectral dichroic mirror 51, the reflection mirror 52 and the vacant hole, the galvanometers 55 and 62 are driven to rotate in accordance with corresponding correction quantities, and respective spectrum image positions on the width variable slits 57 and 64 are corrected.

As a result, with the exciting dichroic mirror being switched to the exciting dichroic mirror 17a, 17b or 17c, even if the spectrum image position on the width variable slit 57 is displaced when switched to the spectral dichroic mirror 51, the reflection mirror 52 or the vacant hole, measurement for each band area can be accurately performed without being affected by this displacement.

It is to be noted that a factor causing a displacement of the spectrum image position is not restricted to an angular shift caused due to switching of the beam splitter turret 16 or the spectral beam splitter turret 50. For example, there can be considered an angular displacement caused when a plurality of types of beam expanders 15 which change beam diameters of laser beam to different beam diameters are prepared in order to switch to any beam expander 15, or an angular displacement caused due to zoom switching in an afocal zoom mode. As a result, an angle of light entering the beam splitter turret 16 is changed and angles of light entering the respective dispersive elements 54 and 61 vary. Moreover, it can be also considered that angles of light entering the respective dispersive elements 54 and 61 vary by switching the confocal lens 21 or the collimator lens 23 to one having a different focal distance. That is, the factor causing a displacement of the spectrum image position includes switching of the optical elements which can be a cause of shifting of angles of light entering the respective dispersion elements 54 and 61.

The respective diffraction gratings 54 and 61 are driven to rotate by using the respective galvanometers 55 and 62. The galvanometers 55 and 62 can perform stable driving at low to high speeds. As a result, each spectrum can be moved in each corresponding spectrum direction at an optimum speed (i.e., at a high speed when the fluorescence is strong and a low speed when it is weak) taking an intensity of the fluorescence to be measured, S/N and a detection time of a detector into consideration.

In order to acquire spectral data, the rotational driving of the galvanometers 55 and 62 which rotate the diffraction gratings 54 and 61 are synchronized with the scanning of the galvanometer 19 which two-dimensionally scans the laser beam. For example, with the galvanometers 55 and 62 being fixed to a given wavelength center, two-dimensional scanning image acquisition corresponding to one frame is performed by using the galvanometer scanner 19.

Then, the galvanometers 55 and 62 are driven to rotate gradually in order to change a wavelength center to be fetched, and two-dimensional image acquisition corresponding to one frame is again carried out by using the galvanometer scanner 19.

Thereafter, the rotational driving of the galvanometers 55 and 62 and the two-dimensional image acquisition using the galvanometer scanner 19 are repeated.

At this moment, driving positions of the galvanometers 55 and 62 are carried out by taking correction quantities of the galvanometers 55 and 62 corresponding to combinations of the respective exciting dichroic mirrors 17a, 17b and 17c, the spectral dichroic mirror 51, the reflection mirror 52 and the vacant hole into consideration, and hence displacements of the spectrum image formation position and the variable slits 57 and 64 are corrected.

By rotating the respective diffraction gratings 54 and 61 every predetermined angles in accordance with one-frame scanning of the laser beam in this manner, the spectral data at each scanning position of the laser beam can be correctly acquired.

The galvanometer scanner 19 is used to scan the laser beam on the sample 9, and the galvanometers 55 and 62 are used for the rotation driving to move a wavelength center. The spectral data can be acquired at a high speed by using the same galvanometers.

As to acquisition of the spectral data, an image is obtained by changing a wavelength in accordance with each one-frame scanning, but scanning may be performed by changing a wavelength in accordance with each one-line scanning. Specifically, the rotational driving of the galvanometers 55 and 62 are effected every time scanning of one line (main scanning) is terminated, and a wavelength center is moved. When acquisition of images each corresponding to one line in all band areas is terminated, scanning (sub-scanning) is performed for one pixel in a direction orthogonal to a main scanning direction using the galvanometer scanner 19. Here, the wavelength center is again moved while effecting the main scanning for one line.

It is to be noted that the respective diffraction gratings 54 and 61 are rotated by driving of the respective galvanometers 55 and 62 in the third embodiment, but the present invention is not restricted thereto, and they may be rotated by using a motor.

It is to be noted that the present invention is not restricted to the first to third embodiments, and it can be modified in many ways without departing from the scope thereof on the embodying stage.

For example, switching between the respective exciting dichroic mirrors 17a, 17b and 17c or switching between the spectral dichroic mirror 51, the reflection mirror 52 and the vacant hole is not restricted to switching based on rotation using, e.g., the splitter turrets 16 and 51, and any other switching mechanism such as switching using a slide mechanism may be used.

In the first embodiment, a position of the variable slit 29 is corrected in the operation to switch between the respective exciting dichroic mirrors 17a, 17b and 17c. The present invention is not restricted thereto, and a position of the variable slit 29 may be corrected in accordance with each correction quantity corresponding to displacement of a spectrum image formation position caused due to, e.g., replacement of the beam expander 15, the confocal lens 21 and the collimator lens 23.

In the second embodiment, the light receiving pixel 41 enabling light reception and the light receiving pixel 41 disabling the same in the line sensor 40 are corrected. The present invention is not restricted thereto, and the light sensor 40 itself may be moved in the spectrum direction in accordance with each correction quantity corresponding to a displacement of the spectrum image formation position.

In the third embodiment, the light are divided into the reflected light and the transmitted light in accordance with each wavelength by using one spectral dichroic mirror 51. The present invention is not restricted thereto, and a spectral dichroic mirror is additionally provided on one or both of the reflected light path R and the transmitted light path T. Based on this structure, one or both of the reflected light and the transmitted light of the spectral dichroic mirror 51 may be further divided. In this case, a spectrum image formation position is displaced by switching of the additionally provided spectral dichroic mirror. Thus, a correction quantity corresponding to this displacement is stored in the memory 33.

The third embodiment is not restricted to rotating the respective diffraction gratings 54 and 61, and the respective width variable slits 57 and 64 may be substituted with the variable slit 29 in the first embodiment. The variable slit 29 is moved in the spectrum direction.

The respective width variable slits 57 and 64 and the respective photodetectors 58 and 56 may be substituted with the line sensor 40 in the second embodiment. In the line sensor 40, the light receiving pixel 41 enabling light reception of light and the light receiving pixel 41 disabling the same are corrected.

There is a possibility that an optical axis angle of light entering the diffraction grating 24 may be changed when replacing the respective optical elements, e.g., the condenser lenses 56 and 63, the galvanometer scanner 19, the reflection mirror 20, the confocal lens 21, the collimator lens 23 and the reflection mirror 59 provided on the light path extending to the position where the fluorescence emitted from the sample 9 enters the respective diffraction gratings 55 and 61, and a spectrum image formation position may be displaced. The memory 33 may store each correction quantity corresponding to each displacement of the spectrum image formation position caused due to replacement of the condenser lenses 56 and 63, the galvanometer scanner 19, the reflection mirror 20, the confocal lens 21, the collimator lens 23 and the reflection mirror 59.

What is claimed is:

1. A scanning laser microscope comprising:
   a laser beam source which outputs laser beam;
   a dispersive element which disperses light emitted from a sample when irradiating the sample with the laser beam and makes spectrum;
   an image formation element which forms an image of the spectrum made by the dispersive element;
   a wavelength band extraction portion which is arranged in the vicinity of the image position of the spectrum formed by the image formation element and extract light in at least one wavelength band from the spectrum;
   at least one photodetector which detects the light in the wavelength band extracted by the wavelength band extraction portion;
   at least one optical element which is selectively arranged between the sample and the dispersive element; and
   a correction portion which corrects a positional relationship between the wavelength band extraction portion and a position of the spectrum image which is displaced in the dispersion direction due to a change in an angle of the light entering the dispersive element caused by switching the optical element.

2. The scanning laser microscope according to claim 1, wherein the optical element includes exciting beam splitters which can separate the light emitted from the sample from the laser beam, and can be switched to each other.

3. The scanning laser microscope according to claim 2, wherein the correction portion previously stores a plurality of correction quantities corresponding to the respective displacements of the spectrum image position relative to each of the exciting beam splitter, and corrects a positional relationship between the spectrum image position and the wavelength band extraction portion in accordance with the correction quantity relative to the exciting beam splitter when switched to this exciting beam splitter.

4. The scanning laser microscope according to claim 3, wherein the wavelength band extraction portion has a variable slit movable in the same direction as the spectrum direction, and
   upon switching the exciting beam splitter, the correction portion moves the variable slit in the spectrum direction in accordance with the correction quantity relative to this exciting beam splitter.

5. The scanning laser microscope according to claim 3, wherein upon switching the exciting beam splitter, the correction portion controls to rotate the dispersive element in accordance with the correction quantity relative to this exciting beam splitter and displaces the spectrum image position in the spectrum direction with respect to the wavelength band extraction portion.

6. The scanning laser microscope according to claim 5, further comprising:
   a scanning portion which scans the laser beam outputted from the laser beam source and irradiates the sample with the laser beam; and
   a synchronization control portion which enables acquisition of spectral data at each of the scanning position on the sample from the light in the wavelength band extracted by the wavelength band extraction portion by synchronizing a scanning operation of the laser beam on the sample by the scanning portion with a rotating operation of the dispersive element,
   wherein the correction portion controls a rotational angle of the dispersive element which is controlled to rotate by the synchronization control portion in accordance with the correction quantity relative to the exciting beam splitter.

7. The scanning laser microscope according to claim 3, wherein the correction portion corrects a positional relationship between the spectrum image position and the wavelength band extraction portion in cooperation with switching of the exciting beam splitter.

8. The scanning laser microscope according to claim 1, wherein the optical element includes spectral beam splitter which divide the light emitted from the sample into respective light according to a plurality of wavelength band.

9. The scanning laser microscope according to claim 8, wherein the correction portion previously stores a plurality of correction quantities corresponding to the respective displacements of the spectrum image position relative to each of the spectral beam splitters, and corrects the positional relationship between the spectrum image position and the wavelength band extraction portion in accordance with the correction quantity relative to the spectral beam splitter when switched to this spectral beam splitter.

10. The scanning laser microscope according to claim 9, wherein the wavelength band extraction portion has a variable slit movable in the same direction as the spectrum direction, and
upon switching the spectral beam splitter, the correction portion moves the variable slit in the spectrum direction in accordance with the correction quantity relative to this spectral beam splitter.

11. The scanning laser microscope according to claim 9, wherein upon switching the spectral beam splitter, the correction portion controls to rotate the dispersive element in accordance with the correction quantity relative to this spectral beam splitter, and displaces the spectrum image position in the spectrum direction with respect to the wavelength band extraction portion.

12. The scanning laser microscope according to claim 11, further comprising:
a scanning portion which scans the laser beam outputted from the laser beam source and irradiates the sample with the laser beam; and
a synchronization control portion which enables acquisition of spectral data at each of the scanning positions on the sample from the light in the wavelength band extracted by the wavelength band extraction portion by synchronizing a scanning operation of the laser beam on the sample by the scanning portion with a rotating operation of the dispersive element,
wherein the correction portion controls a rotational angle of the dispersive element which is controlled to rotate by the synchronization control portion in accordance with the correction quantity relative to the spectral beam splitter.

13. The scanning laser microscope according to claim 9, wherein the correction portion corrects a positional relationship between the spectrum image position and the wavelength band extraction portion in cooperation with switching of the spectral beam splitter.

14. The scanning laser microscope according to claim 1, wherein the optical element includes a plurality of exciting beam splitters which separate light emitted from the sample from the laser beam and can be switched to each other, and a plurality of spectral beam splitters which divide the light emitted from the sample into respective light in accordance with a plurality of wavelength bands.

15. The scanning laser microscope according to claim 14, wherein the correction portion previously stores a plurality of correction quantities corresponding to the respective displacements of the spectrum image position with respect to respective combinations of switching between the plurality of exciting beam splitters and between the plurality of spectral beam splitters, and corrects a positional relationship between the spectrum image position and the wavelength band extraction portion in accordance with the correction quantity relative to one or both of the exciting beam splitter and the spectral beam splitter when one or both of the exciting beam splitter and the spectral beam splitter are switched.

16. The scanning laser microscope according to claim 15, wherein the wavelength band extraction portion has a variable slit movable in the same direction as the spectrum direction, and
when one or both of the exciting beam splitter and the spectral beam splitter are switched, the correction portion moves the variable slit in the spectrum direction in accordance with the correction quantity relative to a combination of the exciting beam splitter and the spectral beam splitter.

17. The scanning laser microscope according to claim 15, wherein, when one or both of the exciting beam splitter and the spectral beam splitter are switched, the correction portion controls to rotate the dispersive element in accordance with the correction quantity relative to a combination of the exciting beam splitter and the spectral beam splitter, and displaces the spectrum image position in the spectrum direction with respect to the wavelength band extraction portion.

18. The scanning laser microscope according to claim 17, further comprising:
a scanning portion which scans the laser beam outputted from the laser beam source and irradiates the sample with the laser beam; and
a synchronization control portion which enables acquisition of spectral data at each of the scanning positions on the sample from the light in the wavelength band extracted by the wavelength band extraction portion by synchronizing a scanning operation of the laser beam on the sample by the scanning portion with a rotating operation of the dispersive element,
wherein the correction portion controls a rotational angle of the dispersive element which is controlled to rotate by the synchronization control portion in accordance with the correction quantity relative to a combination of the exciting beam splitter and the spectral beam splitter.

19. The scanning laser microscope according to claim 15, wherein the correction portion corrects a positional relationship between the spectrum image position and the wavelength band extraction portion in accordance with the correction quantity in cooperation with switching of one or both of the exciting beam splitter and the spectral beam splitter.

20. The scanning laser microscope according to claim 1, wherein the correction portion previously stores a plurality of correction quantities corresponding to the respective displacements of the spectrum image position relative to each of the optical element, and corrects a positional relationship between the spectrum image position and the wavelength band extraction portion in accordance with the correction quantity relative to the optical element when switched to this optical element.

21. The scanning laser microscope according to claim 20, wherein the wavelength band extraction portion has a variable slit movable in the same direction as the spectrum direction, and
upon switching the optical element, the correction portion moves the variable slit in the spectrum direction in accordance with the correction quantity relative to this optical element.

22. The scanning laser microscope according to claim 20, wherein, upon switching the optical element, the correction portion controls to rotate the dispersive element in accordance with the correction quantity relative to this optical element, and displaces the spectrum image position in the spectrum direction with respect to the wavelength band extraction portion.

23. The scanning laser microscope according to claim 22, further comprising:
a scanning portion which scans the laser beam outputted from the laser beam source and irradiates the sample with the laser beam; and
a synchronization control portion which enables acquisition of spectral data at each of the scanning positions on the sample from the light in the wavelength band extracted by the wavelength band extraction portion by synchronizing a scanning operation of the laser beam on the sample by the scanning portion with a rotating operation of the dispersive element,
wherein the correction portion controls a rotational angle of the dispersive element which is controlled to rotate by the synchronization control portion in accordance with the correction quantity relative to the optical element.

24. The scanning laser microscope according to claim 20, wherein the correction portion corrects a positional relationship between the spectrum image position and the wavelength band extraction portion in accordance with the correction quantity in cooperation with switching of the optical element.

25. A scanning laser microscope comprising:
a laser beam source which outputs laser beam;
a dispersive element which disperses light emitted from a sample when irradiating the sample with the laser beam and makes spectrum;
an image formation element which forms an image of the spectrum made by the dispersive element;
a photodetector having a plurality of detection portions each of which detects the light in each wavelength band being arranged in the spectral direction;
at least one optical element which is selectively arranged between the sample and the dispersive element; and
a correction portion which corrects a position of each detection portion which reads a light detection value correspond to the displacement of the position of the spectrum image displaced in the dispersion direction due to a change in an angle of the light which enter the dispersive element by switching the optical element.

26. The scanning laser microscope according to claim 25, wherein the optical elements includes exciting beam splitters which separate light emitted from the sample from the laser beam and can be switched to each other.

27. The scanning laser microscope according to claim 26, wherein the correction portion previously stores a plurality of correction quantities corresponding to the respective displacements of the spectrum image position relative to each of the exciting beam splitters, and corrects a positional relationship between the spectrum image position and a position of the detection portion which reads a light detection value from the photodetector in accordance with the correction quantity relative to the exciting beam splitter when switched to this exciting beam splitter.

28. The scanning laser microscope according to claim 27, wherein the correction portion corrects a positional relationship between the spectrum image position and a position of the detection portion which reads the light detection value in cooperation with switching of the exciting beam splitter.

29. The scanning laser microscope according to claim 25, wherein the optical element includes a plurality of spectral beam splitters which divide the light emitted from the sample into respective light in accordance with a plurality of wavelength band.

30. The scanning laser microscope according to claim 29, wherein the correction portion previously stores a plurality of correction quantities corresponding to each of the displacements of the spectrum image position relative to each of the spectral beam splitters, and corrects a positional relationship between the spectrum image position and a position of the detection portion which reads a light detection value from the photodetector in accordance with the correction quantity relative to the spectral beam splitter when switched to this spectral beam splitter.

31. The scanning laser microscope according to claim 30, wherein the correction portion corrects a positional relationship between the spectrum image position and a position of the detection portion which reads a light detection value from the photodetector in cooperation with switching of the spectral beam splitter.

32. The scanning laser microscope according to claim 25, wherein the plurality of optical elements includes a plurality of exciting beam splitters which separate light emitted from the sample from the laser beam and can be switched to each other, and a plurality of spectral beam splitters which divide the light emitted from the sample into respective light in accordance with a plurality of wavelength bands.

33. The scanning laser microscope according to claim 32, wherein the correction portion previously stores a plurality of correction quantities corresponding to each of the displacements of the spectrum image position with respect to respective combinations of switching between the plurality of exciting beam splitters and between the plurality of spectral beam splitters, and corrects a positional relationship between the spectrum image position and a position of the detection portion which reads a light detection value from the photodetector in accordance with the correction quantity relative to each combination of switching of the exciting beam splitter and the spectral beam splitter when one or both of the exciting beam splitter and the spectral beam splitter are switched.

34. The scanning laser microscope according to claim 33, wherein the correction portion corrects a positional relationship between the spectrum image position and a position of the detection portion which reads a light detection value from the photodetector in cooperation with switching of one or both of the exciting beam splitter and the spectral beam splitter.

35. The scanning laser microscope according to claim 25, wherein the correction portion previously stores a plurality of correction quantities corresponding to each of the displacements of the spectrum image position relative to each of the plurality of optical elements, and corrects a positional relationship between the spectrum image position and a position of the detection portion which reads a light detection value from the photodetector in accordance with the correction quantity relative to the optical element when switched to this optical element.

36. The scanning laser microscope according to claim 35, wherein the correction portion corrects a positional relationship between the spectrum image position and a position of the detection portion which reads a light detection value from the photodetector in cooperation with switching of the optical element.

37. A scanning laser microscope comprising:
a laser beam source which outputs laser beam;
a dispersive element which disperses light emitted from a sample when irradiating the sample with the laser beam and makes spectrum;
an image formation element which forms an image of the spectrum made by the dispersive element;
a photodetector having a plurality of detection portions each of which detects the light in each wavelength band being arranged in the spectral direction;
at least one optical element which is selectively arranged between the sample and the dispersive element; and
a correction portion which moves the photodetector in the same direction as the spectrum direction correspond to the displacement of the position of the spectrum image displaced in the dispersion direction due to a change in an angle of the light which enter the dispersive element by switching the optical element.

38. A scanning laser microscope comprising:
a laser beam source which outputs laser beam;
a plurality of spectral beam splitters which divide the light emitted from a sample into respective light in accordance with a plurality of wavelength band when irradiating the sample with the laser beam;
a plurality of dispersive elements which disperse to spectrums the respective light according to the plurality of wavelength band divided by the plurality of spectral beam splitters;
a plurality of image formation elements each of which forms an image of each of the spectrums dispersed by the plurality of dispersive elements;
a plurality of wavelength band extraction portions which are arranged in the vicinity of respective image formation positions of the respective spectrums image-formed by the plurality of image formation elements, and extracted respective light in at least one wavelength band from the respective spectrums;
a plurality of photodetectors which detect the respective light according to the wavelength band extracted by the plurality of wavelength band extraction portion; and
a correction portion which previously stores a plurality of correction quantities corresponding to each of the displacements of the spectrum image position relative to each of the plurality of spectral beam splitters, controls to rotate the dispersive elements in accordance with the correction quantity relative to the spectral beam splitter when switched to this spectral beam splitter, and corrects the spectrum image positions relative to the wavelength band extraction portions.

* * * * *